United States Patent [19]

LaHann et al.

[11] Patent Number: 4,546,11[?]

[45] Date of Patent: Oct. 8, 198[?]

[54] METHOD FOR PREVENTING OR REDUCING DIPILATORY IRRITATION

[75] Inventors: Thomas R. LaHann, Cleves; Ralph W. Farmer, Maderia, both of Ohio

[73] Assignee: The Procter & Gamble Company, Cincinnati, Ohio

[21] Appl. No.: 557,677

[22] Filed: Dec. 2, 1983

Related U.S. Application Data

[63] Continuation of Ser. No. 330,731, Dec. 14, 1981, abandoned.

[51] Int. Cl.[4] .................... A61K 31/165; A61K 7/155
[52] U.S. Cl. ......................... 514/627; 8/161
[58] Field of Search ............................ 424/324; 8/161

[56] References Cited

U.S. PATENT DOCUMENTS

| | | | |
|---|---|---|---|
| 3,628,910 | 12/1971 | Grayson | 424/71 |
| 4,121,904 | 10/1978 | Schampol | 8/161 |
| 4,313,958 | 2/1982 | LaHann | 424/324 |
| 4,401,663 | 8/1983 | Buckwalter et al. | 424/321 |

OTHER PUBLICATIONS

Merck Index, p. 224.
Kiernan, "A Study of Chemically Induced Acute Inflammation in the Skin of the Rat" *Quart. J. Exp. Physiol.*, vol. 62, (1977), pp. 151-161.
Jansco et al., "Direct Evidence for Neurogenic Inflammation and its Prevention by Denervation and by Pretreatment with Capsaicin," *Br. J. Pharm. Chemother.* vol. 31, (1967), pp. 138-151.
Ariver et al., "Modification by Capsaicin and Compound 40/80 of Dye Leakage Induced by Irritants in the Rat," *Br. J. Pharm.*, vol. 59, (1977), pp. 61-68.
Yaksh et al., "Intrathecal Capsaicin Depletes Substance P in the Rat Spinal Cord and Produces Prolonged Thermal Analgesia," *Science*, vol. 260, (1979), pp. 481-483.
Virus et al., "Pharmacologic Actions of Capsaicin: Apparent Involvement of Substance P and Serotonin,' *Life Sciences*, vol. 24, (1979), pp. 1273-1281.
Bernstein et al., "Bradykinin, Substance P, Prostaglandin $E_2$ and Papain Induced Flare Suppressed by Capsaicin," *Clin. Res.*, vol. 29, No. 4, (1981), p. 787A.

*Primary Examiner*—Albert T. Meyers
*Assistant Examiner*—Freda Abramson
*Attorney, Agent, or Firm*—David K. Dabbiere; Steven J Goldstein; Eric W. Guttag

[57] ABSTRACT

A method for preventing or reducing dermal irritation caused by thioglycolate depilatories by applying capsaicin and/or its salt(s) to at least a portion of the depilated area.

9 Claims, No Drawings

METHOD FOR PREVENTING OR REDUCING DIPILATORY IRRITATION

TECHNICAL FIELD

This is a continuation of application Ser. No. 330,731, filed Dec. 14, 1981, now abandoned.

The present invention relates to a method for preventing or reducing depilatory-caused dermal irritation.

Chemical compositions which attack and disintegrate hair have been in use since ancient times. These compositions typically take advantage of the fact that the disulfide bonds in hair keratin are vulnerable to cleavage by both reducing agents and strongly alkaline solutions. Under the influence of such different chemical agents as alkali metal sulfides and sulfides, cyanides, amines, mercaptans, etc., the S—S bond in keratin breaks, increasing osmotic pressure develops within the hair fiber, and the fiber swells, loses its tensile strength, and generally disintegrates.

Chemical depilatory compositions are convenient, because they destroy hair more deeply than shaving, and therefore can be used less often, and without the risk of cuts or abrasions. Unfortunately, depilatory compositions can cause dermal irritation. This irritation prevents frequent, repeated use of such compositions on the body, particularly on tender mucosal surfaces, and sensitive facial skin. Consequently, the desirability of chemical depilatory compositions has been limited by such irritant side effects. There is thus a need for depilatory systems which are effective in disintegrating unwanted hair, yet relatively non-irritating to skin.

The present invention relates to the discovery that capsaicin and/or its salt(s) are effective in preventing or reducing dermal irritation caused by thioglycolate depilatories. In particular, it has been suprisingly discovered that the application of capsaicin and/or its salt(s) to a portion of the depilated area is also effective to prevent or reduce such irritation in the adjacent depilated area to which capsaicin and/or its salt(s) have not been applied.

BACKGROUND ART

J. A. Kiernan, *Quart. J. of Exp. Physiol.*, (1977) 62 151-161, states that capsaicin N-(3-methoxy-4-hydroxyphenyl-methyl)-8-methyl-6-nonenamide is known to confer resistance to some but not all chemical irritants.

Jancso, et al., *Br. J. Pharmac. Chemother.* (1967), 31, 138-151, states that by repeated administration of capsaicin, ocular and/or cutaneous pain receptors can be desensitized to chemical, but not other, stimuli.

Arvier, et al., *Br. J. Pharm.* (1977), 59, 61-68, indicate that capsaicin reduces or blocks the edema formation associated with certain types of inflammation.

DISCLOSURE OF THE INVENTION

The present invention relates to a method for preventing or reducing the dermal irritation caused by a thioglycolate depilatory agent, which comprises the step of applying to at least a portion of a depilated area an anti-irritant selected from the group consisting of capsaicin, its dermatologically acceptable salt(s) and mixtures of capsaicin and its salt(s) in an amount effective to prevent or reduce irritation caused by treatment of the depilated area with a thioglycolate depilatory agent.

Capsaicin has the following structure:

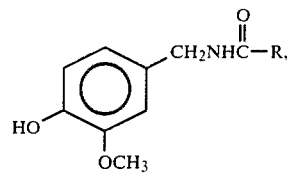

where

R is —(CH$_2$)$_4$CH=CH—CH(CH$_3$)$_2$

Capsaicin can be readily obtained by the ethanol extraction of the fruit of *capsicum frutescens* or *capsicum annum*. It is available commercially from a variety of suppliers, and can also be prepared synthetically by published methods. In some commercially available forms of capsaicin, R=—(CH$_2$)$_7$CH$_3$. This "pseudocapsaicin" is pharmacologically indistinguishable from natural capsaicin. The present invention encompasses the use of both forms, and where the term "capsaicin" is used, both forms are meant.

By "thioglycolate depilatory agent" is meant thioglycolic acid, its alkali metal (e.g. sodium), alkaline earth metal (e.g. calcium), and ammonium salt(s), or mixtures of the acid and its salt(s).

By "an amount effective to prevent or reduce irritation" is meant an amount of capsaicin and/or its salt(s) effective to reduce or prevent the irritation caused by treatment of the depilated area with the thioglycolate depilatory agent at a reasonable benefit/risk ratio. The amount of capsaicin and/or its salt(s) used can vary with the severity of the irritation, the duration of the treatment, the specific formulation employed, the concentration of capsaicin and/or its salt(s) therein, and like factors.

By "dermatologically acceptable salts" is meant those salts of capsaicin which are safe for application to skin tissue. These salts include the sodium, potassium, calcium, magnesium, and ammonium salts.

By "depilated area" is meant that area which is, or is about to be, depilated by treatment with a thioglycolate depilatory agent.

By "applying" is meant the direct laying on or spreading of capsaicin and/or its salt(s) (including dermatologically acceptable compositions containing same) on skin tissue which is, or is about to be, depilated. Capsaicin and/or its salt(s) can be applied before and/or after treatment of the depilated area with the thioglycolate depilatory agent to prevent or reduce irritation caused thereby. Application of capsaicin and/or its salt(s) to the depilated area after treatment with the depilatory agent provides the most effective irritation prevention or reduction, especially when lower concentrations of capsaicin and/or its salt(s) are used. The number of applications needed to provide effective irritation prevention or reduction can depend upon the concentration of capsaicin and/or its salt(s) used, and when capsaicin and/or its salt(s) are applied in relation to the treatment with the depilatory agent. Application of capsaicin and/or its salt(s) soon after depilation, e.g. within about 8 hours, provides the most effective irritation prevention or reduction, especially in conjunction with additional applications on subsequent days. Multiple applications (2 or more sequential, time spaced applications) soon after depilation are particularly effective. The length of time during which capsaicin and/or its salt(s) is left on the depilated area can also determine its effectiveness, especially for single applications thereof. An application duration of at least about 1 hour, preferably from about 2 to about 6 hours, usually provides effective irritation prevention or reduction.

DERMATOLOGICALLY ACCEPTABLE COMPOSITIONS CONTAINING CAPSAICIN AND/OR ITS SALT(S)

Dermatologically acceptable compositions containing capsaicin and/or its salt(s) are especially useful for application to the depilated area to prevent or reduce irritation caused by the depilatory agent. These compositions comprise an effective amount of capsaicin and/or its salt(s), usually at least about 0.5%, and preferably from about 1% to about 2%. High concentrations, e.g., above about 2%, of capsaicin and/or its salt(s) can cause reddening of the skin, as well as a burning sensation, which should be taken into account in formulating such compositions. The balance of the composition comprises a dermatologically acceptable carrier. Suitable carriers for capsaicin and/or its salt(s) preferably remain in place on the skin as a continuous film and resist being washed off easily by perspiration or by immersion in water. Generally, the carrier is organic in nature and capable of having dispersed or dissolved therein capsaicin and/or its salt(s). Lotions, creams, solutions, and gels are common physical forms of such compositions. A more detailed description of such forms follows.

All percentages herein are by weight of the composition unless otherwise specified.

A. Lotions

Suitable lotions comprise an effective amount of capsaicin and/or its salt(s), from about 1% to about 25%, preferably from about 3% to about 15%, of an emollient, the balance being water, a $C_2$ or $C_3$ alcohol, or a mixture of water and the alcohol. Numerous emollients are known. Examples of such emollients are as follows:

1. Hydrocarbon oils and waxes. Examples are mineral oil, petrolatum, paraffin, ceresin, ozokerite, microcrystalline wax, polyethylene, and perhydrosqualene.

2. Silicone oils, such as dimethylpolysiloxanes, methylphenylpolysiloxanes, water-soluble and alcohol-soluble silicone-glycol copolymers.

3. Triglyceride fats and oils such as those derived from vegetable and animal sources. Examples include castor oil, safflower oil, cotton seed oil, corn oil, olive oil, cod liver oil, almond oil, avocado oil, palm oil, sesame oil, and soybean oil.

4. Acetoglyceride esters, such as acetylated monoglycerides.

5. Ethoxylated glycerides, such as ethoxylated glyceryl monostearate.

6. Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

7. Alkenyl esters of fatty acids having 10 to 20 carbon atoms. Examples thereof include oleyl myristate, oleyl stearate, and oleyl oleate.

8. Fatty acids having 10 to 20 carbon atoms. Suitable examples include pelargonic, lauric, myristic, palmitic, stearic, isostearic, hydroxystearic, oleic, linoleic, ricinoleic, arachidic, behenic, and erucic acids.

9. Fatty alcohols having 10 to 20 carbon atoms. Lauryl, myristyl, cetyl, hexadecyl, stearyl, isostearyl, hydroxystearyl, oleyl, ricinoleyl, behenyl, erucyl, and 2-octyl dodecyl alcohols are examples of satisfactory fatty alcohols.

10. Fatty alcohol ethers. Ethoxylated fatty alcohols of 10 to 20 carbon atoms include the lauryl, cetyl, stearyl, isostearyl, oleyl, and cholesterol alcohols having attached thereto from 1 to 50 ethylene oxide groups or 1 to 50 propylene oxide groups, or a mixture thereof.

11. Ether-esters such as fatty acid esters of ethoxylated fatty alcohols.

12. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohol linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.

13. Polyhydric alcohols and polyether derivatives. Propylene glycol, dipropylene glycol, polypropylene glycol (M.W. 2000–4000), polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol (M.W. 200–6000), methoxy polyethylene glycols 350, 550, 750, 2000, 5000, poly[ethylene oxide] homopolymers (M.W. 100,000–5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol), $C_{15}$–$C_{18}$ vicinal glycol, and polyoxypropylene derivatives of trimethylolpropane are examples thereof.

14. Polyhydric alcohol esters. Ethylene glycol mono- and di-fatty acid esters, diethylene glycol mono- and di-fatty acid esters, polyethylene glycol (M.W. 200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glycerol monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

15. Wax esters such as beeswax, spermaceti, myristyl myristate, stearyl stearate.

16. Beeswax derivatives, e.g. polyoxyethylene sorbitol beeswax. These are reaction products of beeswax with ethoxylated sorbitol of varying ethylene oxide content, forming a mixture of ether-esters.

17. Vegetable waxes including carnauba and candelilla waxes.

18. Phospholipids such as lecithin and derivatives.

19. Sterols. Cholesterol, cholesterol fatty acid esters are examples thereof.

20. Amides such as fatty acid amides, ethoxylated fatty acid amides, solid fatty acid alkanolamides.

The lotions further comprise from about 1% to about 10%, preferably from about 2% to about 5%, of an emulsifier. The emulsifiers can be of a nonionic, anionic or cationic class. Examples of satisfactory nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene glycol wherein the fatty acid moiety contains from 10 to 20 carbon atoms, fatty acid monoglycerides wherein the fatty acid moiety contains from 10 to 20 carbon atoms, diethylene glycol, polyethylene glycols of molecular weight 200 to 6000, propylene glycols of molecular weight 200 to 3000, glycerol, sorbitol, sorbitan, polyoxyethylene sorbitol, polyoxyethylene sorbitan, and hydrophilic wax esters. Suitable anionic emulsifiers include the fatty acid soaps, e.g. sodium, potassium and triethanolamine soaps, wherein the fatty acid moiety contains from 10 to 20 carbon atoms. Other suitable anionic emulsifiers include the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units. Satisfactory cationic emulsifiers are the quaternary ammonium, morpholinium and pyridinium compounds. Certain of the emollients described in preceding paragraphs also have emulsifying properties. When a lotion is formulated containing such an emollient, an additional emulsifier is not needed, although it can be included.

The balance of the lotion is water, a $C_2$ or $C_3$ alcohol, or a mixture of water and the alcohol. The lotions are formulated by simply admixing all of the components together. Preferably capsaicin and/or its salt(s) are dissolved in the mixture. Optional components such as the emulsifier or common additives can be included. One common additive is a thickening agent at a level from about 1% to about 10% of the composition. Examples of suitable thickening agents include: cross-linked carboxypolymethylene polymers, ethyl cellulose, polyethylene glycols, gum tragacanth, gum kharaya, xanthan gums and bentonite.

B. Creams

Suitable creams comprise an effective amount of capsaicin and/or its salt(s), from about 5% to about 50%, preferably from about 10% to about 25%, of an emollient, the balance being water. The emollients previously described for lotions are also used in the creams. Optionally the cream form contains a suitable emulsifier, as previously described for lotions. When an emulsifier is included, it is in the cream at a level from about 3% to about 50%, preferably from about 5% to about 20%.

C. Solutions

Suitable solution forms comprise an effective amount of capsaicin and/or its salt(s), the balance being a suitable organic solvent. Suitable organic materials useful as the solvent or a part of a solvent system are propylene glycol, polyethylene glycol (M.W. 200–600) polypropylene glycol (M.W. 425-2025), glycerine, sorbitol esters, 1,2,6-hexanetriol, ethanol, isopropanol, diethyl tartrate, butanediol, and mixtures thereof. Such solvent systems can also contain water.

These compositions in solution form can be applied to the skin as is, or else can be formulated into an aerosol and applied to the skin as a spray-on. The compositions in the aerosol form further comprise from about 25% to about 80%, preferably from about 30% to about 50% of a suitable propellant. Examples of such propellants are the chlorinated, fluorinated and chlorofluorinated lower molecular weight hydrocarbons. Nitrous oxide, carbon dioxide, butane, and propane are also used as propellant gases. These propellants are used at levels sufficient to expel the contents of the container.

D. Gels

Compositions herein can be formulated into a gel form by simply admixing a suitable thickening agent to the previously described solution compositions. Examples of suitable thickening agents have been previously described with respect to the lotions.

The gelled compositions comprise an effective amount of capsaicin and/or its salt(s), from about 5% to about 75%, preferably from about 10% to about 50%, of an organic solvent as previously described with respect to solutions; from about 0.5% to about 20%, preferably from about 1% to about 10%, of the thickening agent; the balance being water.

Additives commonly found in topical compositions such as preservatives, e.g. methyl and ethyl-paraben, dyes, and perfume can be included in any of the previously described compositions.

SPECIFIC ILLUSTRATIONS OF INVENTION

The following examples provide specific illustrations of the present invention but are not limiting thereof:

EXAMPLE 1

(Different Capsaicin Materials)

Groups of 8 male Sprague-Dawley rats weighing 90-115 grams were used for testing the effectiveness of capsaicin and pseudocapsaicin in preventing or reducing depilatory irritation. The animals were clipped and depilated with Nair ®, a commercially available thioglycolate depilatory. The test compositions (2% capsaicin or pseudocapsaicin in an isotonic saline solution containing 48% ethyl alcohol and 4% Tween 80) or a control composition (same as test compositions but without capsaicin or pseudocapsaicin) were applied to one quadrant (Treated Area) of the depilated area once, 2 hours after depilation on the first day; four times, 2 hours apart on the second day; and three times, 2 hours apart on the third day for a total of eight applications. The duration of each application was 2 hours. The remaining three quadrants of the depilated area were left untreated (Untreated Area). Oral ingestion was prevented by the use of "Elizabethan" collars. On the fourth day, the animals were depilated a second time and evaluated for irritation four hours later.

Irritation scores for each animal were determined by visual inspection (evaluator was unaware of particular treatment of animal) using the following subjective evaluation scale:

| Score | Description of Irritation |
| --- | --- |
| 0 | No irritation |
| 0.5 | No scab formation, faint white scale |
| 1.0 | Scab formation (pale orange/orange) over less than 10% of area |
| 2.0 | Mild to moderate intensity scab formation (pale |

-continued

| Score | Description of Irritation |
|---|---|
| | orange) over 10–33% of area |
| 3.0 | Mild to moderate intensity scab formation (pale orange) over 33–75% of area |
| 3.5 | Moderate intensity scab formation (pale orange, occasional deep orange/red) over 75–90% of area |
| 4.0 | Moderate to severe intensity scab formation (deep orange, occasional pale orange) over 90–100% of area |
| 5.0 | Severe intensity scab formation (deep orange/red) over 100% of area |

The irritation scores were totaled for each of the 8-animal groups, the maximum cumulative score being 40. A cumulative score of less than 8 indicated a minimal level of irritation; a score of 8–24 indicated a higher, but acceptable level of irritation; a score of above 24 indicated an unacceptable level of irritation. The results from this testing were as follows:

| | Cumulative Score | |
|---|---|---|
| Test Composition | Treated Area | Untreated Area |
| Control | 32.0 | 32.0 |
| Capsaicin | 0 | 1.5 |
| Pseudocapsaicin | 0 | 0.5 |

As can be seen from the above Table, capsaicin or pseudocapsaicin provided very effective irritation prevention or reduction in both the Treated and Untreated Areas.

EXAMPLE 2

(Different Application Schedules)

Different application schedules of a 2% capsaicin composition were tested for effectiveness in preventing or reducing depilatory irritation. The remaining test format (depilation, composition formulation, duration of capsaicin application, determination of irritation score, etc.) was similar to that of Example 1. The results from this testing are as follows:

| | | | | Cumulative Score | |
|---|---|---|---|---|---|
| Schedule No. | When Applied | | | Treated Area | Untreated Area |
| | Day 1* | Day 2** | Day 3** | | |
| Control | — | — | — | 32.0 | 29.0 |
| 1 | 0.5 hr. | 1X | 1X | 3.0 | 3.0 |
| 2 | 2 hr. | 1X | 1X | 0.5 | 4.0 |
| 3 | 5 hr. | 1X | 1X | 3.0 | 5.5 |
| 4 | 8 hr. | 1X | 1X | 3.0 | 4.0 |
| 5 | 2, 4, 6 hr. | — | — | 4.0 | 6.0 |
| 6 | — | 3X | — | 11.0 | 14.0 |
| 7 | — | — | 3X | 26.5 | 27.5 |

*time after depilation.
**number of applications; multiple application were at 2 hr. intervals.

As can be seen from the above Table (No. 1 to 4) single applications of capsaicin to the depilated area on the first day, followed by subsequent single applications on the second and third days, provided very effective irritation prevention or reduction in both the Treated and Untreated Areas. Multiple applications on the first day (No. 5) also provided very effective irritation prevention or reduction in both the Treated and Untreated Areas. Multiple applications on the second day (No. 6) provided acceptable but less effective irritation prevention or reduction in both the Treated and Untreated Areas; multiple applications on the third day (No. 7) provided unacceptable irritation prevention or reduction in both the Treated and Untreated Areas.

EXAMPLE 3

(Different Amounts of Capsaicin, Application Before and After Depilation)

The application of different amounts of capsaicin both before and after depilation was tested for effectiveness in preventing or reducing depilatory irritation. Compositions containing different concentrations of capsaicin were applied three times at 2 hour intervals either before or after depilation. The remaining test format (depilation, composition formulation, duration of capsaicin application, determination of irritation score, etc.) was similar to that of Example 1. The results from this testing are as follows:

| | Cumulative Score | |
|---|---|---|
| When Applied | Treated Area | Untreated Area |
| After Depilation | | |
| Control | 34.0 | 33.0 |
| 1% capsaicin | 11.0 | 17.0 |
| 2% capsaicin | 1.0 | 2.0 |
| Before Depilation | | |
| Control | 33.0 | 31.5 |
| 1% capsaicin | 20.5 | 21.5 |
| 2% capsaicin | 20.0 | 18.5 |
| 4% capsaicin | 22.0 | 21.0 |
| 8% capsaicin | 10.0 | 11.5 |

As can be seen from the above Table, an increase in the capsaicin concentration generally provided more effective irritation prevention or reduction in both the Treated and Untreated Areas. As can also be seen, application of capsaicin after depilation provided more effective irritation prevention or reduction in the Treated and Untreated Areas.

EXAMPLE 4

(Duration of Application)

Single applications of a 2% capsaicin composition left on the depilated area for different lengths of time were tested for effectiveness in preventing or reducing depilatory irritation. The remaining test format (depilation, composition formulation, determination of irritation score, etc.) was similar to that of Example 1. The results from this testing are as follows:

| | | Cumulative Score | |
|---|---|---|---|
| Composition | Duration (hr.) | Treated Area | Untreated Area |
| Control | 2 | 32.0 | 32.0 |
| Capsaicin | 1 | 16.5 | 18.0 |
| Capsaicin | 2 | 8.5 | 10.0 |
| Capsaicin | 6 | 2.0 | 3.0 |

As can be seen from the above Table, increasing the duration of the capsaicin application improved irritation prevention or reduction in the Treated and Untreated Areas.

What is claimed is:

1. A method for preventing or reducing the dermal irritation caused by a thioglycolate depilatory agent, which comprises the step of applying to at least a portion of the depilated area an anti-irritant selected from the group consisting of capsaicin, its dermatologically acceptable salt(s), or mixtures of capsaicin and its salt(s)

in an amount effective to prevent or reduce the irritation caused by treatment of the depilated area with a thioglycolate depilatory agent.

2. A method according to claim 1 wherein a dermatologically acceptable composition containing the anti-irritant is applied.

3. A method according to claim 2 wherein the composition contains at least about 0.5% of the anti-irritant.

4. A method according to claim 3 wherein the composition contains from about 1 to about 2% of the anti-irritant.

5. A method according to claim 1 wherein the anti-irritant is applied after treatment of the depilated area with the depilatory agent.

6. A method according to claim 5 wherein the anti-irritant is capsaicin.

7. A method according to claim 1 wherein a single application of the anti-irritant is left on the depilated area for at least about 1 hour.

8. A method according to claim 7 wherein the anti-irritant is left on the depilated area for from about 2 to about 6 hours.

9. A method according to claim 1 wherein the anti-irritant is capsaicin.

* * * * *